US010799265B2

(12) United States Patent
Graziani (10) Patent No.: US 10,799,265 B2
(45) Date of Patent: Oct. 13, 2020

(54) RE-ENTRY DEVICE FOR PERIPHERAL ARTERIAL RECANALIZATION PROCEDURES

(71) Applicant: Lanfroi Graziani, Brescia (IT)

(72) Inventor: Lanfroi Graziani, Brescia (IT)

( * ) Notice: Subject to any disclaimer, the term of this patent is extended or adjusted under 35 U.S.C. 154(b) by 202 days.

(21) Appl. No.: 15/668,753

(22) Filed: Aug. 4, 2017

(65) Prior Publication Data

US 2019/0038311 A1 Feb. 7, 2019

(51) Int. Cl.
*A61B 17/34* (2006.01)
*A61M 25/01* (2006.01)
(Continued)

(52) U.S. Cl.
CPC .......... *A61B 17/3421* (2013.01); *A61B 17/22* (2013.01); *A61B 17/3478* (2013.01); *A61M 25/0041* (2013.01); *A61M 25/0194* (2013.01); *A61M 29/02* (2013.01); *A61B 2017/00331* (2013.01); *A61B 2017/22038* (2013.01); *A61B 2017/22061* (2013.01); *A61B 2017/22095* (2013.01); *A61B 2017/3454* (2013.01);
(Continued)

(58) Field of Classification Search
CPC . A61B 17/22; A61B 17/3421; A61B 17/3478; A61B 2017/00331; A61B 2017/22038; A61B 2017/22061; A61B 2017/22095; A61B 2017/3454; A61M 25/0041; A61M 25/0102; A61M 25/0194; A61M 29/02; A61M 2025/0004; A61M 2025/0197
See application file for complete search history.

(56) References Cited

U.S. PATENT DOCUMENTS 3,633,580 A * 1/1972 Knox .................. A61M 5/3286
604/274
5,607,394 A * 3/1997 Andersen ............ A61M 25/104
604/102.01
(Continued)

FOREIGN PATENT DOCUMENTS

WO 2009/144561 A2 12/2009

OTHER PUBLICATIONS

International Search Report and Written Opinion of the International Searching Authority for International Patent Application No. PCT/IB2018/055858 dated Oct. 17, 2018, 14 pages.
(Continued)

*Primary Examiner* — Jocelin C Tanner
(74) *Attorney, Agent, or Firm* — Merchant & Gould P.C.

(57) ABSTRACT

A re-entry device (1) for recanalization procedures of an arterial vessel by an intraluminal or subintimal technique includes a catheter (10) having a distal end (12) with a curved tip (13) by an angle ($\alpha$) of between 30° and 90°, and an angled-tip stylet (2) insertable into the inner lumen of the catheter (10) to exit from a distal opening (14) thereof. The angled-tip stylet (2) is metal and has a distal end (22) with a curved tip (23) ending in a sharped apex (24). The distal end (22) of the an angled-tip stylet (2) is tapered and has a length of 3-5 cm, and the curved tip (23) is bent by an angle ($\beta$) of between 30° and 50°. The structure makes the apex (24) adjustable outside the two-dimensional plane defined by the curved tip (13) of the catheter (10) to facilitate penetration of the arterial wall.

24 Claims, 5 Drawing Sheets (51) Int. Cl.
*A61M 29/02* (2006.01)
*A61B 17/22* (2006.01)
*A61M 25/00* (2006.01)
*A61B 17/00* (2006.01)

(52) U.S. Cl.
CPC . *A61M 25/0102* (2013.01); *A61M 2025/0004* (2013.01); *A61M 2025/0197* (2013.01)

(56) References Cited

U.S. PATENT DOCUMENTS

| | | | | |
|---|---|---|---|---|
| 2005/0054983 | A1* | 3/2005 | Mullen | A61B 17/3415 604/164.02 |
| 2008/0015625 | A1* | 1/2008 | Ventura | A61B 17/3439 606/191 |
| 2010/0298737 | A1* | 11/2010 | Koehler | A61B 10/0275 600/567 |
| 2012/0035615 | A1* | 2/2012 | Koester | A61B 17/3468 606/129 |
| 2013/0006232 | A1* | 1/2013 | Pellegrino | A61B 17/3472 606/33 |
| 2015/0032141 | A1* | 1/2015 | Silvestro | A61B 17/3478 606/185 |
| 2015/0257774 | A1* | 9/2015 | Galdonik | A61B 17/221 606/127 |
| 2015/0320975 | A1* | 11/2015 | Simpson | A61M 25/0041 604/510 |

OTHER PUBLICATIONS

Trocar—an overview, ScienceDirect Topics, 13 pages, printed Jul. 31, 2019, https://www.sciencedirect.com/topics/nursing-and-health-professions/trocar.

Standard laparascopic trocars for the treatment of tension pneumothorax: A superior alternative to needle decompression, Quinton Hatch et al., J. Trauma Acute Car Surg., vol. 77, No. 1, Copyright 2014, 6 pages.

* cited by examiner

RE-ENTRY DEVICE FOR PERIPHERAL ARTERIAL RECANALIZATION PROCEDURES

BACKGROUND OF THE INVENTION

The present invention refers to a medical device for the recanalization of occluded arterial vessels, especially in lower peripheral districts.

The present invention can be used in surgery and particularly in minimally invasive procedures, such as endovascular recanalization in challenging areas where the space of manoeuvre is significantly reduced and reaching the target area requires specific skills.

In particular, the device object of the invention, is intended for use in revascularization procedures in peripheral districts through intraluminal or subintimal technique.

As well known in the medical field, a chronic total occlusion (CTO) is an obstruction within an arterial lumen, reduces the blood flow within the vessel itself. In some cases it may be difficult if not impossible to pass through such occlusion with a medical device, from an anterograde or retrograde direction, in order to recanalize the vessel. The nature of the occlusion may be markedly calcified making the use of normal guide wires having a diameter of 0.014; 0.018 or 0.035 ineffective. If direct crossing is impossible, special guide wire techniques have been developed for the creation of a subintimal path (that is, a path through the medial-intimal layer of the arterial vessel wall) that passes outside the occlusion, then returns into the true lumen of the vessel in a point distal to the occlusion, so creating a path suitable to restore the normal blood flow.

In some cases, the re-entry in the true lumen from the subintimal space can be difficult without the use of a recanalization devices so making easier and safer the re-entry.

SUMMARY OF THE INVENTION

The aim of the present invention is to solve the problems related to the current state-of-the-art devices also considering specific safety requirements.

BRIEF DESCRIPTION OF THE DRAWINGS

Further features and advantages of the invention will appear more clearly from the detailed description of a preferred, non-exclusive embodiment, shown by way of a non-limiting example with the aid of the accompanying drawings, in which.

DETAILED DESCRIPTION OF THE PREFERRED EMBODIMENTS

As shown in the above figures, reference numeral 1 indicates as a whole a re-entry device for recanalization procedures of an arterial vessel through subintimal technique according to the present invention.

Figure 2:
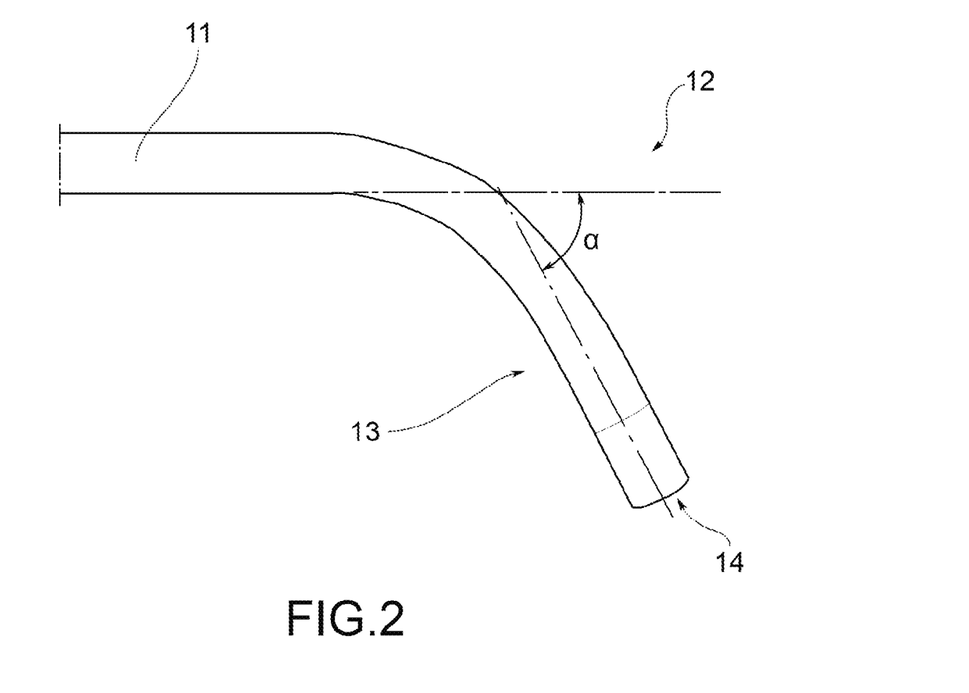
FIG. 2 shows a perspective view of the distal portion of a guide catheter as part of the re-entry device according to the present invention.
Figure 4:
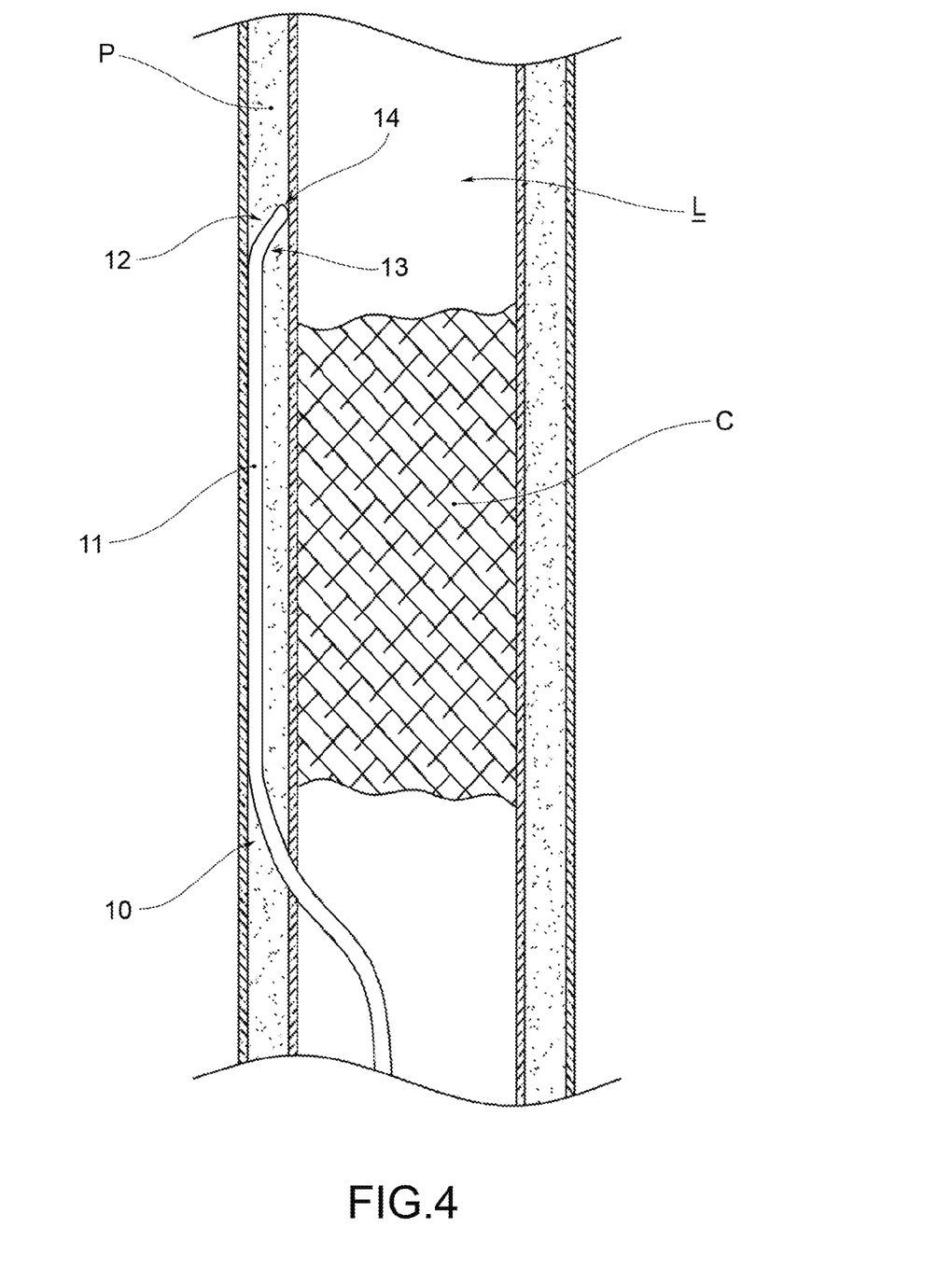
FIG. 4 shows the re-entry device during an occlusion (CTO) crossing.

The re-entry device 1 comprises a catheter 10, shown in FIGS. 2 and 4.

Catheter 10 is configured to be advanced on a traditional guide wire (not shown) to reach the site of intervention that needs to be re-vascularized. Preferably, the catheter 10 is an OTW (over-the-wire) type having an inner lumen 17 extending across the entire length of catheter 10.

Catheter 10 comprises a body 11 extending from a proximal portion (not shown) to a distal end 12.

Body 11, or a portion thereof, is a braided polyamide extruded body having one or more internal inner lumens and preferably one or more side holes.

The distal end 12 of catheter 10, well illustrated in FIG. 2, comprises a curved tip 13 ending in a distal opening 14 through which an angled-tip stylet 2 is intended to protrude.

Figure 5A:
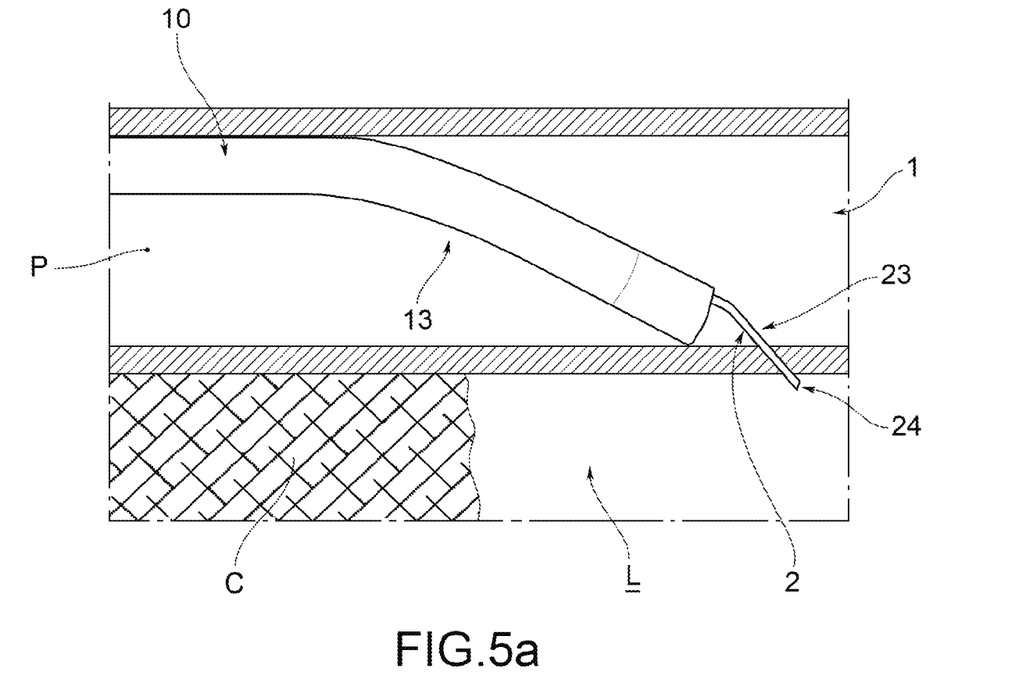
FIGS. 5A and 5B show the re-entry device during use, particularly the re-entry of stylet tip into the true lumen of the arterial vessel, beyond the occlusion.
Figure 5B:
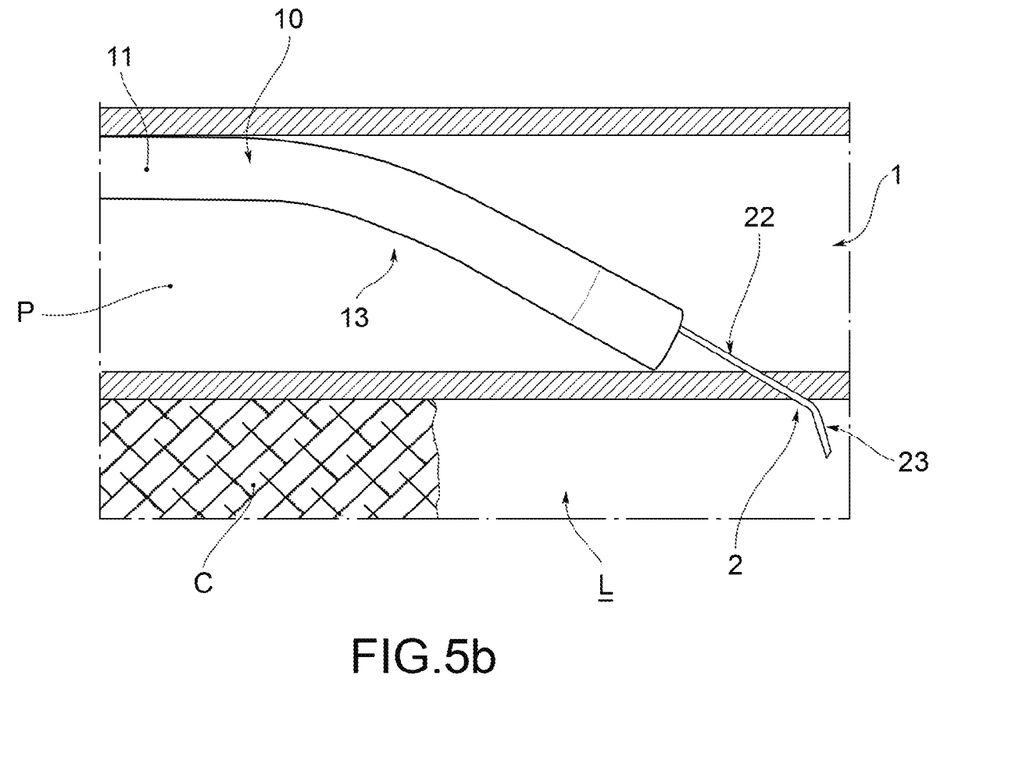

Catheter 10 is in fact internally provided with an inner lumen 17, extending from the proximal portion to the distal end 12, up to the distal opening 14. A angled-tip stylet 2 is then intended to be inserted into catheter 10, slide along the inner lumen 17 of the catheter 10, up to exit from the distal opening 14, as shown in FIGS. 5A and 5B.

Preferably, the curved tip 13 is bent by an angle α with respect to the longitudinal axis of catheter 10. Preferably, at rest, or in the absence of an angled-tip stylet 2 inserted into the curved tip 13, angle α is of between 30° and 90°, preferably 60°.

The distal end 12 is partially flexible, i.e. able to deform. In particular, the curved tip 13 changes its bending degree when an angled-tip stylet 2 is advanced therein.

Advantageously, the curved tip 13 of catheter 10 still retains a minimum angle of curvature (i.e. it does not straighten up completely) also in the presence of an angled-tip stylet 2 inserted therein. Preferably, the minimum angle α is about 30° (FIGS. 5A and 5B). This technical feature allows guiding the angled-tip stylet 2 in the correct direction, i.e. facing towards the vessel wall to be penetrated to return into the true lumen of the vessel.

Figure 3A:
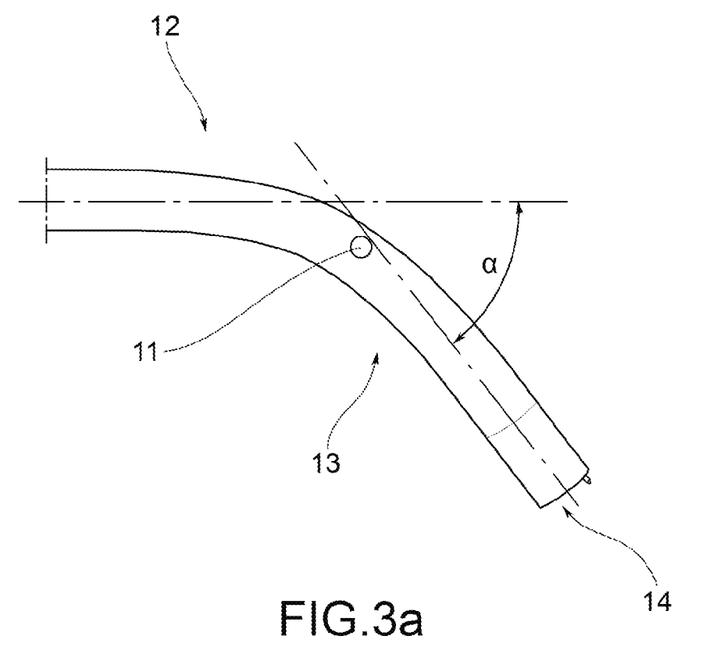
FIGS. 3A and 3B show the re-entry device during use for a re-entry and particularly the direction of the guide catheter curved tip as function of the needle retraction inside it.
Figure 3B:
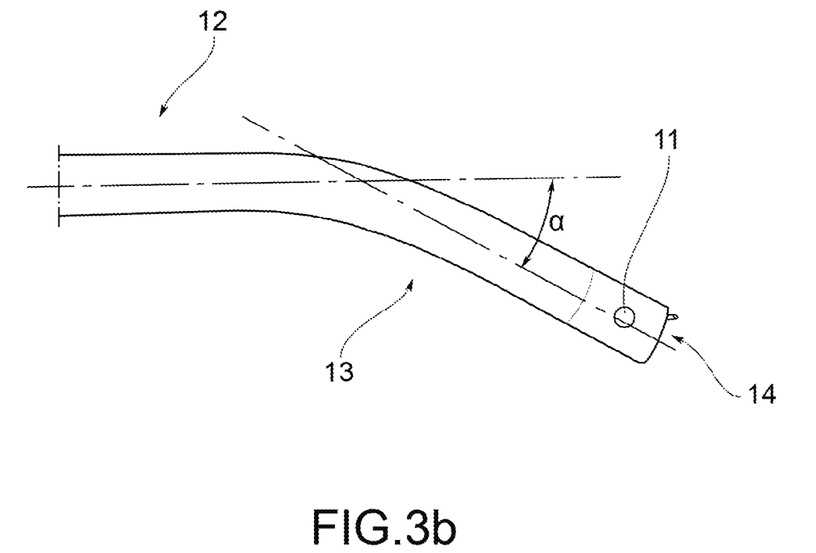

As shown in FIGS. 3A and 3B (where the distal end of the angled-tip stylet 2 is indicated with a circle), the advancement of the angled-tip stylet 2 causes a partial straightening of the curved tip 13. Preferably, the advancement of the angled-tip stylet 2 in the curved tip 13 causes a variation of angle α of about 30°.

In an embodiment example, angle α measures at rest (FIG. 2) about 60°; advancing the angled-tip stylet 2, the angle α decreases to 50° (FIG. 3A) and gradually up to about 30° (FIG. 3B).

Figure 1:
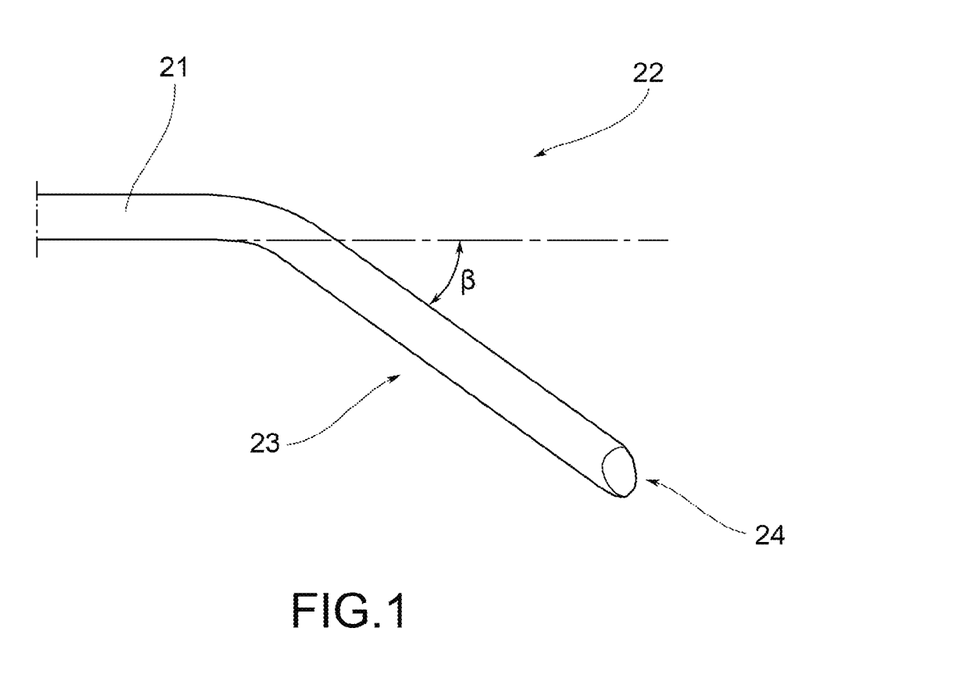
FIG. 1 shows a perspective view of the distal portion of an angled-tip stylet as part the re-entry or, alternatively, intraluminal crossing device according to the present invention.

The re-entry device 1 further comprises an angled-tip stylet e 2, whose distal end 22 is shown in FIG. 1.

The angled-tip stylet 2 is configured to be advanced within catheter 10 to reach the site of intervention that needs to be revascularized.

The angled-tip stylet 2 comprises a body 21 extending from a proximal portion (not shown) to a distal end 22 (FIG. 1). The body 21 has a circular section.

Body 21 is a solid body made of metal. The angled-tip stylet 2 is made of stainless steel, preferably austenitic in an alloy with chromium-nickel. For example, the metal alloy of which the angled-tip stylet is made of about 70% Iron, 20% Chromium, 8% Nickel, 1% Silicon and 1% Manganese. Since the material used to make body 21 determines the flexibility, support and manoeuvrability of the angled-tip stylet 2, the choice to use steel (stainless steel) allows achieving a more easily manoeuvrable and stiffer stylet.

Preferably, body 21 of the angled-tip stylet 21 has a Teflon (PTFE) coating.

Body 21 of the angled-tip stylet 2 has an outer diameter in inches of 0.018 in or in millimeters of 0.45 mm or 0.014 in, i.e. 0.35 mm. Considering that the larger the diameter, the greater the support provided, a 0.018 in body 21 ensures better rotation capability (torquability) of the angled-tip stylet 2.

Preferably, the angled-tip stylet 2 has an overall length of about 200.

The distal end 22 of the angled-tip stylet 2 is tapered, i.e. the diameter is reduced towards the distal tip. In particular, the outer diameter decreases by about 45%. For example, in the case of a 0.018 in body 21, the outer diameter changes from 0.45 mm to 0.20 mm at apex 24. Considering that the penetration capacity of the distal end 22 of the angled-tip stylet 2 is a function of its rigidity and its cross sectional area, a minimum diameter of 0.20 mm imparts greater thrust force to traverse the vessel wall and to return into the true lumen.

Moreover, the tapered distal end 22 has a length of between 3 cm and 5 cm, preferably 4 cm. Considering that the distal end of the angled-tip stylet 2 is the most flexible portion that affects the maneuverability thereof, a shortened distal end increases the transmission of force and makes the angled-tip stylet 2 more manoeuvrable.

The distal end 22 of the angled-tip stylet 2, well illustrated in FIG. 1, comprises a curved tip 23 ending in an apex 24.

Preferably, the curved tip 23 is bent by an angle β with respect to the longitudinal axis of the angled-tip stylet 2. Preferably, angle β is of between 30° and 50°, preferably between 40° and 45°. This technical feature allows easily directing apex 24 of the angled-tip stylet in the desired direction, i.e. facing towards the vessel wall to be penetrated in order to return into the true lumen of the vessel.

Apex 24 of the curved tip 23 of the angled-tip stylet 2 is sharp to facilitate the penetration of the vessel wall.

Figure 6:
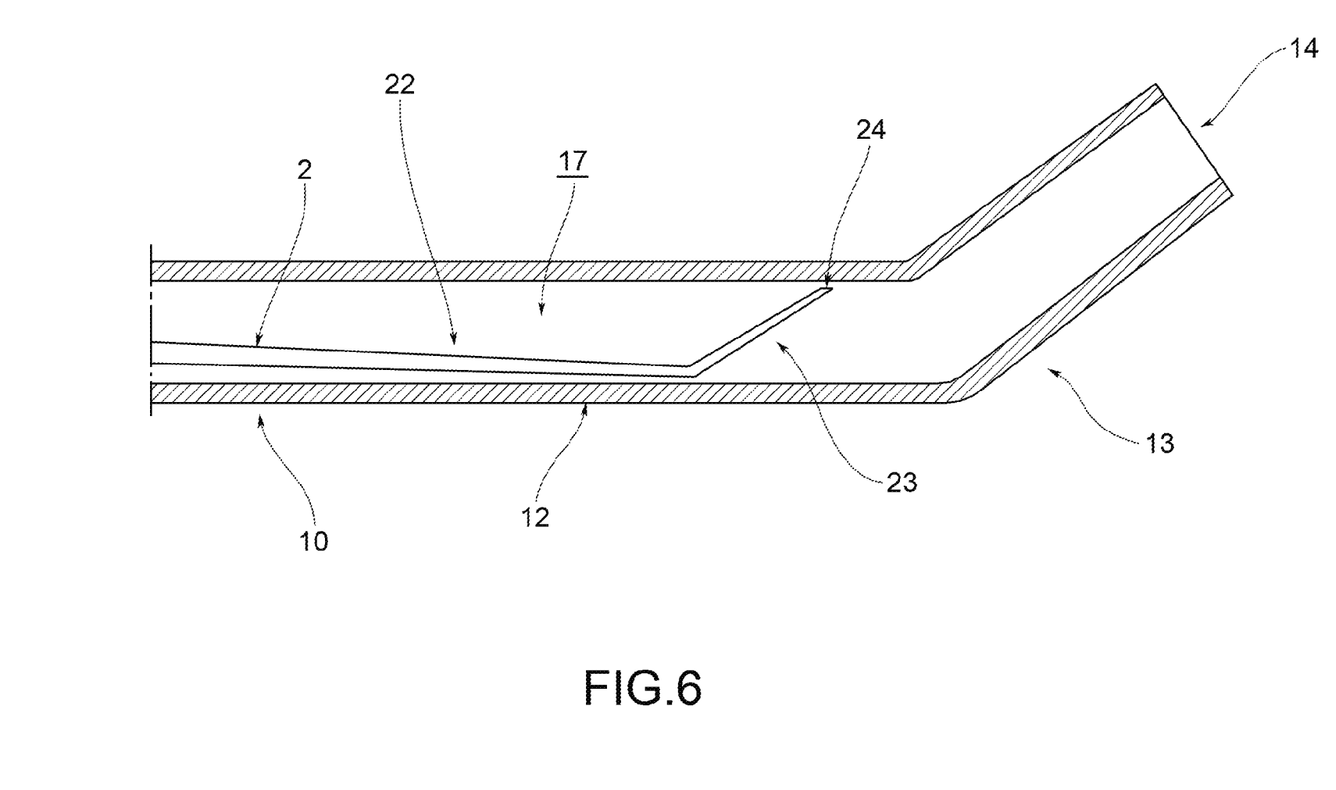
FIG. 6 shows the angled-tip stylet 2 inserted into the inner lumen of the catheter 10.

Apex 24 of the curved tip 23 of the angled-tip stylet 2 may have different geometries: conical, rounded, pyramid. Preferably, the sharped angle of apex 24 is oriented parallel to the longitudinal axis of body 21 of the angled-tip stylet 2 (as shown in FIG. 6), to do not penetrate into the wall of the inner lumen 17 of the catheter during the advancement.

Preferably, the curved tip 23 of the angled-tip stylet 2 has a Teflon (PTFE) coating, an extension of the coating applied on body 21.

Preferably, the curved tip 23 of the angled-tip stylet 2 has a coating of a radiopaque, abrasion-resistant metal material, such as platinum or gold.

Preferably, the distal end 22 of the angled-tip stylet is devoid of radiopaque hydrophilic polymer coating so preventing such a coating from detachment when directing apex 24 to reach the lumen of the vessel.

The re-entry device 1 can therefore operate along a two-dimensional plane (2D) if the curved tip 23 of the angled-tip stylet 2 is in the same plane as the curved tip 13 of catheter 10 (as shown in FIGS. 5A and 5B).

However, unlike known devices, since the angled-tip stylet 2 is provided with its own torquability even when inserted within lumen 17 of catheter 10, the curved tip 23 provided with sharped apex 24 may be in turn directed towards the desired direction, also outside the two-dimensional plane in which the curved tip 13 of catheter is. The re-entry device 1 is therefore a three-dimensional system (3D) in which catheter 10 imparts to the angled-tip stylet 2 a first direction in the plane, but in which the angled-tip stylet 2 itself can be oriented taking three-dimensional advancement properties. This technical feature, absent in the known and commercially available re-entry systems, greatly increases the direction possibilities and facilitates the re-entry into the true vessel lumen beyond the occlusion. This capability is further improved by the crossability (ability to cross the stenosis) and pushability (ability to transmit thrust) features of the angled-tip stylet 2, along with its great penetration capability provided by the stiff sharped curved tip 23.

It is noted that the angled-tip stylet 2 is designed in particular for peripheral revascularization procedures: it is provided with a larger diameter that ensures greater capacity of rotation; it is made of a material (stainless steel) making it easily manoeuvrable; it has a short distal end that increases the transmission of force and has a high penetration capacity.

In an embodiment example, the re-entry device 1 comprises:

- a catheter 10 having outer diameter 4 Fr (i.e. 1.35 mm), inner diameter 0.042 in (i.e. 1 mm), length 100 cm, with curved tip 13 with angle α of between 45° and 90°, with braided body 11;
- an angled-tip stylet 2 having a body 21 with 0.018 in or 0.014 in outer (0.45 mm or 0.35 mm), made of stainless steel (preferably austenitic in allow with chromium-nickel), with tapered distal end 22 for a length of 4 cm, curved tip 23 with angle β of 45°, sharped apex 24.

The re-entry technique is now described in the peripheral arterial recanalization with subintimal technique, through anterograde homolateral femoral route using a re-entry device 1 comprising a catheter 10 and an angled-tip stylet 2 as described above.

The recanalization technique of a peripheral arterial vessel by sub-intimal route is routinely used in extended occlusions, also with varying degrees of calcification.

Through anterograde femoral route, a catheter 10 is advanced towards the beginning of occlusion C as described above and depicted in FIGS. 2 and 4 (i.e., an angiographic catheter, provided with support, angled tip, 4 F or 1.35 mm), on a first guide wire (i.e. steel, with outer Teflon-coated coil, flexible straight tip, gauge 0.035 in or 0.89 mm).

The occlusion is tested using short advancing movements of the traditional guide wire until resistance is encountered that prevents the correct advancement thereof.

The first guide wire is then replaced with a second guide wire (made of nitinol, with hydrophilic polymer coating, flexible J-curved tip, preferably of 1.5 mm radius, gauge 0.035 in; or for tibial arteries, with stiff guide wire, 0.014 in gauge with hydrophilic polymer tip).

The advancement of the second guide wire in the occlusion leads to the bending of the distal floppy end of the guide wire itself, so forming a loop due to the increased flexibility of the distal segment thereof.

The loop of the distal end of the second guide wire travels into the thickness of the arterial wall of the occluded vessel tract, virtually between the intimae and the adventitia, ideally beneath the intima.

During the advancement, if at the end of the occluded vessel has a large lumen without significant calcification of the arterial wall, the loop of the second guide wire is usually able to spontaneously jump into the true lumen.

Unfortunately this lucky event cannot be predicted with certainty, depending on the degree of fibrosis and calcification of the vessel segment at the end of the occlusion which prevents the immediate return.

In this case, the loop of the second guide wire is advanced up to the level where the lumen is reconstituted, followed by the support catheter 10.

The second guide wire is then removed and an angled-tip stylet 2 according to the invention is inserted into the catheter 10 (gauge 0.018 in or 0.014 in).

The tip of catheter 10 is then oriented towards the vessel lumen with the distal opening 14 facing the arterial wall to be punctured in order to return into the lumen L.

The angled-tip stylet 2 is then advanced within catheter to reach the distal end 12 thereof. The further advancement of the angled-tip stylet 2 inside the curved tip 13 of catheter 10 modifies the bending thereof up to reach the minimum angle α (e.g. 30°). The correct position of the tip is verified using angiograms at a mutual angle of 90°.

Keeping catheter 10 in place, the angled-tip stylet 2 is advanced (in the plane of the curved tip 13) up to exit from the distal opening 14 of catheter 10.

Due to its high torqueability, the angled-tip stylet 2 can be oriented along three dimensions (also outside the plane of the curved tip 13) so as to be easily directed towards the wall of the vessel to be pierced to return into lumen L (FIG. 5A). The angled-tip stylet 2 is then rotated to direct the tip 23 thereof along different planes then those of catheter 10 so as to cross the subintimal space, reach the vessel lumen and advance by a few centimeters along the same.

The angled-tip stylet 2 easily pierces, due to the short, hard curved tip 23 provided with sharp apex 24, the part of the vessel and penetrates lumen L of the vessel.

At this point, once the access to lumen L of the vessel has been achieved, catheter 10 can be removed, and a dilatation catheter (over-the-wire or rapid exchange type) with short balloon (for example with a diameter of between 2 mm and 4 mm and length of about 3-6 cm) is fitted on the angled-tip stylet 2 (from the proximal direction) and advanced up to reach the tip of the angled-tip stylet 2. If the advance thereof is too difficult, the balloon is inflated to expand the path towards the lumen of the vessel.

At this point, the angled-tip stylet 2 is replaced with a support guide wire (such as coronary, with soft tip, gauge 0.014 in or 0.018 in) to reach the Popliteal or Tibial tract and used for a greater dilatation of the path with a balloon catheter having greater length and diameter.

If the artery to be treated is femoral or popliteal, catheter 10 according to the invention is again fitted onto this guide wire, then the support guide wire is replaced with an exchange guide wire (0.035 in). At this point, catheter 10 is again removed and a dilatation catheter (such as over-the-wire type) with long balloon (for example, with a diameter of about 5-6 mm and length of 20 cm) is inserted in its place and inflated to complete the procedure according to the operator's choices.

The present invention also relates to a peripheral arterial vessel recanalization method by sub-intimal route using a re-entry device 1 as described and represented above. This method involves the following steps:

advancing catheter 10 into the thickness of the arterial wall of the occluded vessel tract, up to the level where the lumen is reconstituted and adjusting the tip of catheter 10 so that the distal opening 14 is facing the arterial wall to be pierced to return into lumen L;

advancing an angled-tip stylet 2 into lumen 17 of catheter 10 up to the distal tip 12 thereof;

changing the bending of the curved tip 13 of catheter 10 up to reach the minimum angle α;

making the angled-tip stylet 2 exit from the distal opening 14 of catheter 10 and directing it three-dimensionally towards the vessel wall up to pierce, through the curved tip 23 provided with sharped apex 24, the part of the vessel and penetrate into lumen L of the vessel;

completing the recanalization of the vessel.

Moreover, such a recanalization method, in order to advance catheter 10 into the thickness of the arterial wall of the occluded vessel tract, provides for the following steps:

advancing catheter 10 through anterograde femoral route towards the beginning of occlusion C on a first guide wire (steel, Teflon-coated outside, flexible straight tip, gauge 0.035 in);

replacing the first guide wire with a second guide wire (nitinol, hydrophilic polymer coating, flexible J-curve tip, gauge 0.035 in);

advancing the second guide wire into the occlusion until its distal end bends, thus forming a loop which travels into the thickness of the arterial wall of the occluded tract of the vessel up to the level where the lumen is reconstituted.

removing the second guide wire.

Moreover, such a recanalization method, in order to complete the recanalization of the vessel, provides for the following steps:

removing catheter 10 and fitting a short balloon dilatation catheter on the angled-tip stylet 2;

inflating the balloon to expand the path towards the lumen of the vessel;

replacing the angled-tip stylet 2 with a support guide wire (soft tip, gauge 0.014 in or 0.018 in) to reach the popliteal or tibial tract.

Moreover, if the artery to treat is femoral or popliteal, the method finally provides for:

removing the dilatation catheter and fitting catheter 10 according to the invention on the support guide;

replacing the support guide wire with a change guide wire (0.035 in);

removing catheter 10 and fitting a long balloon dilatation catheter on the support guide wire 2;

inflating the balloon to complete the vessel recanalization.

It is noted that in order to meet the safety requirements, it is important that prior to each advancement of the angled-tip stylet 2, the correct direction of the curved tip 23 must be checked by two orthogonal projections (90°) with contrast medium injection from the femoral introducer sheath.

It is also noted that the use of the re-entry technique through contralateral femoral route (crossover) is not recommended due to the numerous curves that the system would have, which dos not allow a safe and predictable directionality thereof, thus exposing to the risk of complications. The latter, which would possibly be determined by an instrument having a diameter slightly greater (0.35 mm) or less than twice (0.45 mm) than an insulin needle (0.27 mm), which is the smallest needle available, would obviously be very little, if non-existing.

Innovatively, a re-entry device 1 according to the present invention is a system orientable three-dimensionally that allows rapid advance towards the true lumen of the vessel.

Advantageously, a re-entry device 1 according to the present invention can be used in revascularization procedures in peripheral districts through subintimal technique, thus facilitating the penetration step of the vessel wall for a correct return into the true lumen beyond the occlusion and making it safer.

It is clear that a man skilled in the art might make changes and variations to the re-entry system described above, all falling within the scope of protection as defined in the following claims.

The invention claimed is:

1. A re-entry device for arterial vessel recanalization procedures by an intraluminal or subintimal technique, comprising:
   a catheter with a body extending from a proximal portion to a distal end; said body having an inner lumen ending distally in a distal opening; said distal end being provided with a curved tip at an angle of between 30° and 90° with respect to a longitudinal axis of the body;
   an angled-tip stylet configured to be inserted into the inner lumen of the catheter to exit from the distal opening, having a body of a metal material, extending from a proximal portion to a distal end; said distal end comprising a tip ending in a sharp apex;
   wherein said distal end of the angled-tip stylet is tapered and has a length of between 3 cm and 5 cm, and the tip is bent by an angle of between 30° and 50° with respect to the longitudinal axis of the body so that the apex of the angled-tip stylet is independently adjustable outside the two-dimensional plane defined by the curved tip of the catheter in order to facilitate the penetration of the arterial wall;
   wherein the curved tip of the distal end of the catheter is configured to partially straighten during advancement of the angled-tip stylet in the inner lumen of the catheter, and wherein the curved tip of the distal end of the catheter is configured to retain a minimum angle of curvature of about 30° in the presence of the angled-tip stylet inserted in the inner lumen of the catheter for guiding the angled-tip stylet facing towards the wall to be penetrated;
   wherein the tip of the angled-tip stylet is three-dimensionally directable independently of the catheter when the tip of the angled-tip stylet extends beyond the distal opening of the catheter.

2. Re-entry device according to claim 1, wherein the body of the angled-tip stylet is a solid body, made of stainless steel.

3. Re-entry device according to claim 1, wherein the body of the angled-tip stylet has an outer diameter of 0.45 mm or 0.35 mm.

4. Re-entry device according to claim 1, wherein an outer diameter of the distal end of the angled-tip stylet decreases by about 45%.

5. Re-entry device according to claim 1, wherein an outer diameter of the distal end of the angled-tip stylet decreases from 0.45 mm to 0.20 mm at the apex.

6. Re-entry device according to claim 1, wherein the tapered distal end of the angled-tip stylet has a length of about 4 cm.

7. Re-entry device according to claim 1, wherein the angle of the tip of the angled-tip stylet is between 40° and 45°.

8. Re-entry device according to claim 1, wherein advance of the angled-tip stylet into the tip of the catheter causes a reduction of the angle by about 30°.

9. Re-entry device according to claim 1, wherein the angle of the curved tip of the catheter is about 60° when the angled-tip stylet is inserted into the inner lumen of the catheter.

10. The re-entry device according to claim 1, wherein the sharp apex forms a surface parallel to the longitudinal axis of the catheter body when the angled-tip stylet is inserted into the inner lumen of the catheter.

11. A peripheral arterial vessel recanalization method by sub-intimal route by a re-entry device for arterial vessel recanalization procedures, the re-entry device comprising:
    a catheter with a body extending from a proximal portion to a distal end; said body having an inner lumen ending distally in a distal opening; said distal end being provided with a curved tip bent by at an angle of between 30° and 90° with respect to a longitudinal axis of the body;
    an angled-tip stylet configured to be inserted into the inner lumen of the catheter to exit from the distal opening, having a body of a metal material, extending from a proximal portion to a distal end; said distal end comprising a tip ending in a sharp apex;
    wherein said distal end of the angled-tip stylet is tapered and has a length of between 3 cm and 5 cm, and the tip of the stylet is bent by an angle of between 30° and 50° with respect to the longitudinal axis of the body so that the apex of the angled-tip stylet is also adjustable outside the two-dimensional plane defined by the tip of the catheter in order to facilitate the penetration of the arterial wall;
    the method comprising the steps of:
       advancing the catheter into a thickness of an arterial wall of an occluded vessel tract, up to a level where the lumen is reconstituted and adjusting the curved tip of the catheter so that the distal opening is facing the arterial wall to be pierced to return into the lumen;
       advancing an angled-tip stylet into the lumen of the catheter up to the distal tip of the stylet;
       changing the bending of the curved tip of the catheter up to reach a minimum angle;
       making the tip of the angled-tip stylet exit from the distal opening of the catheter and directing the tip of the stylet three-dimensionally towards the vessel wall up to pierce with the sharp apex part of the vessel and penetrate into the lumen of the vessel;
       completing the recanalization of the vessel.

12. Recanalization method according to claim 11, wherein to advance the catheter into the thickness of the arterial wall of the occluded vessel tract, performing the following steps:
    advancing on a first guide wire the catheter through anterograde femoral route towards a beginning of occlusion;
    replacing the first guide wire with a second guide wire;
    advancing the second guide wire into the occlusion until a distal end bends, forming a loop which travels into the thickness of the arterial wall of the occluded vessel tract of the vessel up to the level where the lumen is reconstituted;
    removing the second guide wire.

13. Recanalization method according to claim 12, wherein the first guide wire comprises nitinol, hydrophilic polymer coating, a flexible J-curve tip, and has a gauge of 0.035 in.

14. Recanalization method according to claim 11, wherein to complete the vessel recanalization, performing the following steps:
    removing the catheter and fitting a short balloon dilatation catheter on the angled-tip stylet;
    inflating the balloon to expand a path towards the lumen of the vessel;
    replacing the angled-tip stylet with a support guide wire to reach a popliteal or tibial tract.

15. Recanalization method according to claim 14, wherein if the vessel to treat is a femoral or popliteal artery, the method finally comprises:

removing the dilatation catheter and fitting the catheter on the support guide wire;

replacing the support guide wire with a change guide wire;

removing the catheter and fitting a long balloon dilatation catheter on the support guide wire;

inflating the balloon to complete the vessel recanalization.

16. Recanalization method according to claim 15, wherein the change guide wire has a diameter of 0.035 in.

17. Recanalization method according to claim 14, wherein the support guide wire comprises a soft tip and has a gauge of 0.014 in or 0.018 in.

18. Recanalization method according to claim 14, wherein the change guide wire has a diameter of 0.035 in.

19. Re-entry device according to claim 1, wherein the body of the angled-tip stylet is a solid body made of austenitic stainless steel in an alloy with chromium-nickel.

20. The re-entry device according to claim 1, wherein the apex of the tip of the angled-tip stylet is conical, rounded or pyramidal.

21. The re-entry device according to claim 1, wherein the body of the angled-tip stylet has an outer diameter of 0.018 in or 0.014 in.

22. A method of peripheral arterial vessel recanalization by an intraluminal route by a re-entry device, for arterial vessel recanalization procedures, the re-entry device comprising:

a catheter with a body extending from a proximal portion to a distal end; said body having an inner lumen ending distally in a distal opening; said distal end being provided with a tip curved at an angle of between 30° and 90° with respect to a longitudinal axis of the body;

an angled-tip stylet configured to be inserted into the inner lumen of the catheter to exit from the distal opening, having a body of a metal material, extending from a proximal portion to a distal end; said distal end comprising a tip ending in a sharp apex;

wherein said distal end of the angled-tip stylet is tapered and has a length of between 3 cm and 5 cm, and the tip of the stylet is bent by an angle of between 30° and 50° with respect to the longitudinal axis of the body so that the apex of the angled-tip stylet is further adjustable outside the two-dimensional plane defined by the tip of the to facilitate penetration of the arterial wall;

the method comprising the steps of:

advancing the catheter towards a beginning of occlusion on a first guide wire;

testing the occlusion using short advancing movements of the first guide wire until resistance is encountered that prevents correct advancement of the first guide wire;

replacing the first guide wire with the angled-tip stylet;

advancing the angled-tip stylet into the lumen of the catheter up to a distal tip of the angled-tip stylet;

changing bending of the curved tip of the catheter up to reach a minimum angle;

directing the tip of the angled-tip stylet to exit from the distal opening of the catheter and directing the tip of the stylet three-dimensionally towards the occlusion;

performing the recanalization of the vessel by an intraluminal technique.

23. The method according to claim 22, further comprising performing the following steps:

removing the catheter and fitting a balloon dilatation catheter on the angled-tip stylet;

inflating the balloon to expand a path towards the lumen of the vessel;

replacing the angled-tip stylet with a support guide wire to reach a popliteal tract or a tibial tract.

24. The method according to claim 23, wherein if the vessel being treated is a femoral artery or popliteal artery, the method further comprises:

removing the dilatation catheter and fitting the catheter on the support guide wire;

replacing the support guide wire with a change guide wire;

removing the catheter and fitting a balloon dilatation catheter on the support guide wire;

inflating the balloon to complete the vessel recanalization.

* * * * *